United States Patent [19]
Ramsey et al.

[11] Patent Number: 4,705,947
[45] Date of Patent: Nov. 10, 1987

[54] PULSED HELIUM IONIZATION DETECTION SYSTEM

[75] Inventors: Roswitha S. Ramsey; Richard A. Todd, both of Knoxville, Tenn.

[73] Assignee: The United States of America as represented by the United States Department of Energy, Washington, D.C.

[21] Appl. No.: 721,339

[22] Filed: Apr. 9, 1985

[51] Int. Cl.[4] .......................................... G01N 27/66
[52] U.S. Cl. .................................. 250/386; 250/384; 250/381
[58] Field of Search ............... 250/386, 382, 384, 381; 324/465, 464

[56] References Cited

U.S. PATENT DOCUMENTS

| 3,154,680 | 10/1956 | Greene | 250/381 |
| 3,634,754 | 1/1972 | Lovelock | 250/382 |
| 4,025,794 | 5/1977 | Lovelock | 250/384 |
| 4,117,332 | 9/1978 | Felton et al. | 250/386 |
| 4,137,453 | 1/1979 | Siegel | 250/382 |
| 4,538,066 | 8/1985 | Carle et al. | 250/374 |
| 4,567,368 | 1/1986 | Well et al. | 250/386 |

FOREIGN PATENT DOCUMENTS 1088976 11/1967 United Kingdom ................ 250/384

OTHER PUBLICATIONS

Andrawes et al., Anal. Chem., 52 (1980) 891, "Saturation Region of HID for Gas-Solid ... Chromat".
Lovelock, J., Anal. Chem., 35 (1963), 474, "Electron Absorp. Det. and Techn. ... for Chromat".

Primary Examiner—Carolyn E. Fields
Assistant Examiner—Richard Hanig
Attorney, Agent, or Firm—David E. Breeden; Stephen D. Hamel; Judson R. Hightower

[57] ABSTRACT

A helium ionization detection system is provided which produces stable operation of a conventional helium ionization detector while providing improved sensitivity and linearity. Stability is improved by applying pulsed dc supply voltage across the ionization detector, thereby modifying the sampling of the detectors output current. A unique pulse generator is used to supply pulsed dc to the detector which has variable width and interval adjust features that allows up to 500 V to be applied in pulse widths ranging from about 150 nsec to about dc conditions.

4 Claims, 4 Drawing Figures

PULSED HELIUM IONIZATION DETECTION SYSTEM

This invention is a result of a contract with the United States Department of Energy.

BACKGROUND OF THE INVENTION

This invention relates generally to the art of helium ionization detectors and more specifically to improvements in helium ionization detectors.

The helium ionization detector (HID) is one of the most sensitive detectors currently available for gas chromatography. The detector is nonselective, meaning that it is capable of responding to all chromatographable species ranging from the permanent gases to complex organic molecules. Despite its universal response mechanism and high ionization efficiency, the HID detector has not been widely used. The reasons for its limited use include the stringent requirements for high sensitivity operation, instability, and variations in response for selected species as a function of chromatographic conditions. The greatest sensitivity is obtained when ultrapure helium is used as the carrier gas and when contributions from the chromatographic system (e.g., column bleed) to the background current are minimal. Low parts-per-billion concentrations of the permanent gases can be determined under these conditions.

The universal response characteristic which is largely an advantage can also be troublesome since any atmospheric diffusion in the system will reduce the sensitivity of the detector. Long periods of time may be required to stabilize the detector on initial start-up, when changing separation columns, or following any exposure of the system to the atmosphere. The response to the substrate or solvent used in the column may also be excessively large requiring long periods between sample analyses to allow the detector to return to initial background conditions. When the detector is overloaded by high concentrations of an analyte, or if the background is high, anomalous peak shapes or polarity inversions may be obtained making it difficult to interpret the results.

Despite these problems, there has been renewed interest in the HID. The characteristic negative responses for the permanent gases have been examined and the conditions which invert the signals defined. It was also determined that the detector could be operated in the saturation region of the field intensity with sensitivities comparable to those which can be obtained in the exponential region (i.e., at greater than 350 V). This is due to a decrease in noise level and background current. These reductions in turn have allowed gas-liquid partition columns to be used with the detector which extends the applications to include higher molecular weight organics.

Thus, it will be seen that there is a need for an improved HID system which provides stable operation of an HID while improving the sensitivity and linearity of the device.

SUMMARY OF THE INVENTION

In view of the above need it is an object of this invention to provide an improved HID system which produces stable operation of a conventional HID while providing improved sensitivity and linearity.

Another object of this invention is to provide an improved, stable HID wherein the detector current is sampled in a discontinuous mode by applying bias voltage pulses of selected duration across the detector.

Other objects and many of the attendant advantages of the present invention will be obvious from the following detailed description of a preferred embodiment of the invention taken in conjunction with the drawings.

Briefly, the invention pertains to a pulse operated helium ionization detector system. A conventional helium ionization detector in a flowthrough detecting arrangement is combined with a bias voltage pulse generator with variable pulse width, amplitude and interval adjust to operate the detector in a pulsed bias voltage mode to reduce noise and background current levels in the detectors output current response as compared to conventional dc bias operation.

In accordance with one aspect of the invention, the pulse generator is of a unique design which provides a switching capability operable over a voltage range from 0 to 500 V at less than 1 kHz up to 333 kHz at the highest voltage. The pulse generator allows operation of the detector at higher than conventional bias voltages in the pulsed mode without cell current breakdown thus, extending the sensitive range of the detector.

DETAILED DESCRIPTION OF THE INVENTION

Figure 1:
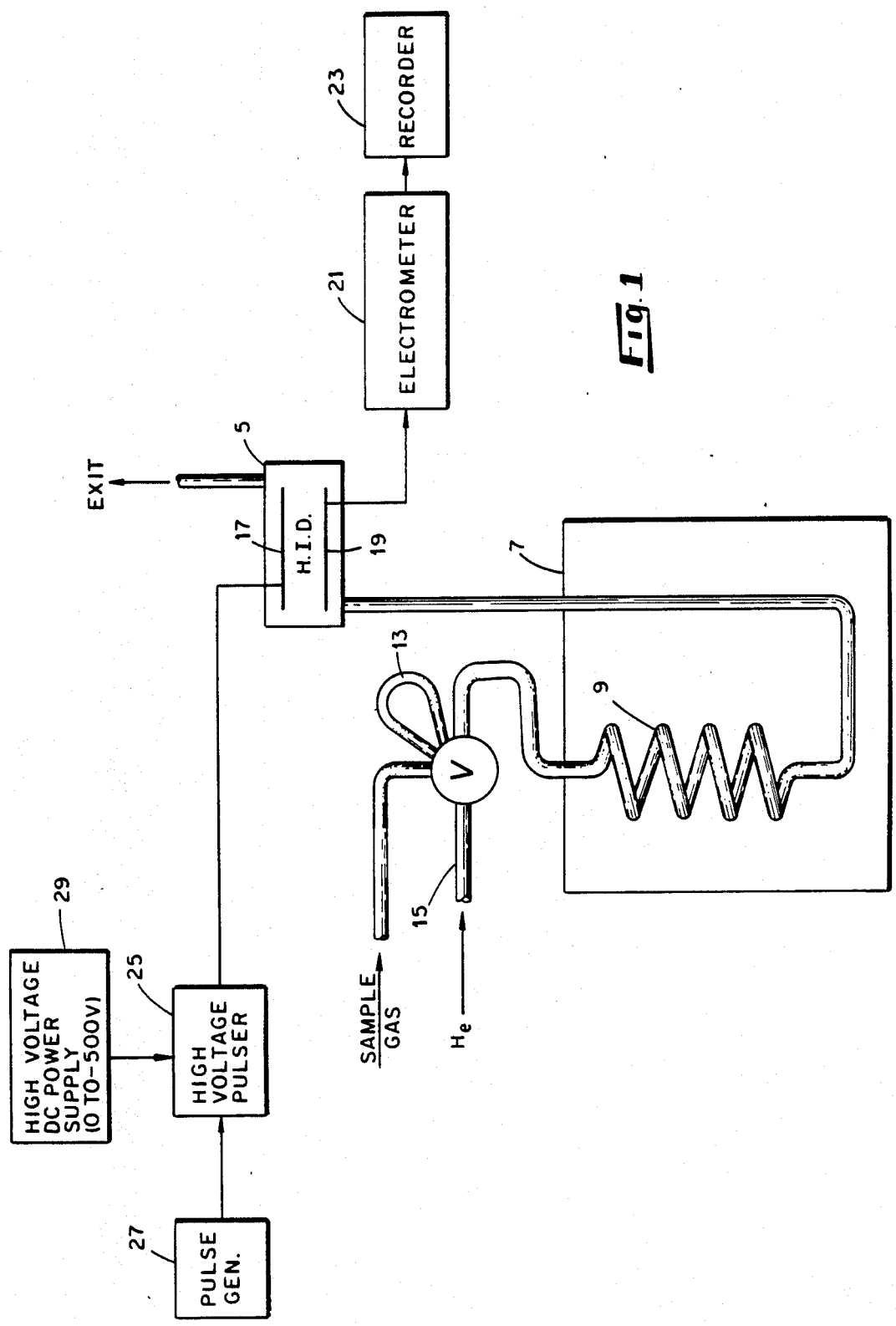
FIG. 1 is a block diagram of a pulsed helium ionization detection system according to the present invention.

Referring now to FIG. 1, there is shown a pulsed helium ionization detection system according to the present invention in which a conventional helium ionization detector (HID) 5, such as the Valco Model 100 H available from Valco Instruments Co., Inc., Houston, Texas, is operated in a pulsed mode to detect components of a gas sample introduced into the detector from a separating column 9 operated within a chromatographic oven 7. Sample gas is injected onto the analytical column 9 through a valved inlet conduit 13. When the valve is switched, the sample gas trapped in the inlet conduit is swept onto the column by the helium carrier gas which is introduced continuously through an inlet conduit 15. Components of the sample gas are separated in the column 9 following injection in a conventional manner and then passed through the HID 5 for detection.

The detector 5 includes a cathode electrode 17 and an anode electrode 19 between which the gas flows through the detector. The anode 19 is formed of a foil containing a radioactive source, such as 1 Ci scandium tritide, which serves to ionize the sample gas components in the detector volume. An electrometer 21 is connected to the anode 19 to measure the detector ionization current which is recorded in a recording device 23, such as a strip chart recorder connected to the output of the electrometer 21.

Pulses having a selected amplitude, pulse width and interval are applied to the cathode from a high voltage pulser 25. The pulse width and frequency are controlled by a pulse generator 27 connection to a control input of the pulser 25. The pulse amplitude is controlled by applying a selected negative dc reference voltage to the switching input of the pulser 25 from a variable, high voltage, dc power supply 29.

Qn a particular embodiment, employing a Kepco model #APH 500M, Flushing, NY, as the power supply 29 and a Global Specialties Model 4001, New Haven, CT, transistor-to-transistor (TTL) pulse generator 27, the high voltage pulser is capable of providing up to 500 V negative pulses with widths ranging from 150 nsec to dc conditions at 500 V. The pulses are limited to a maximum frequency of 333 kHz at 500 V due to the current limitations of the high voltage power supply (40 mA) and the power dissipation in the output devices of the pulser 25. At lower voltages, however, it can be operated at slightly higher frequencies.

Figure 2:
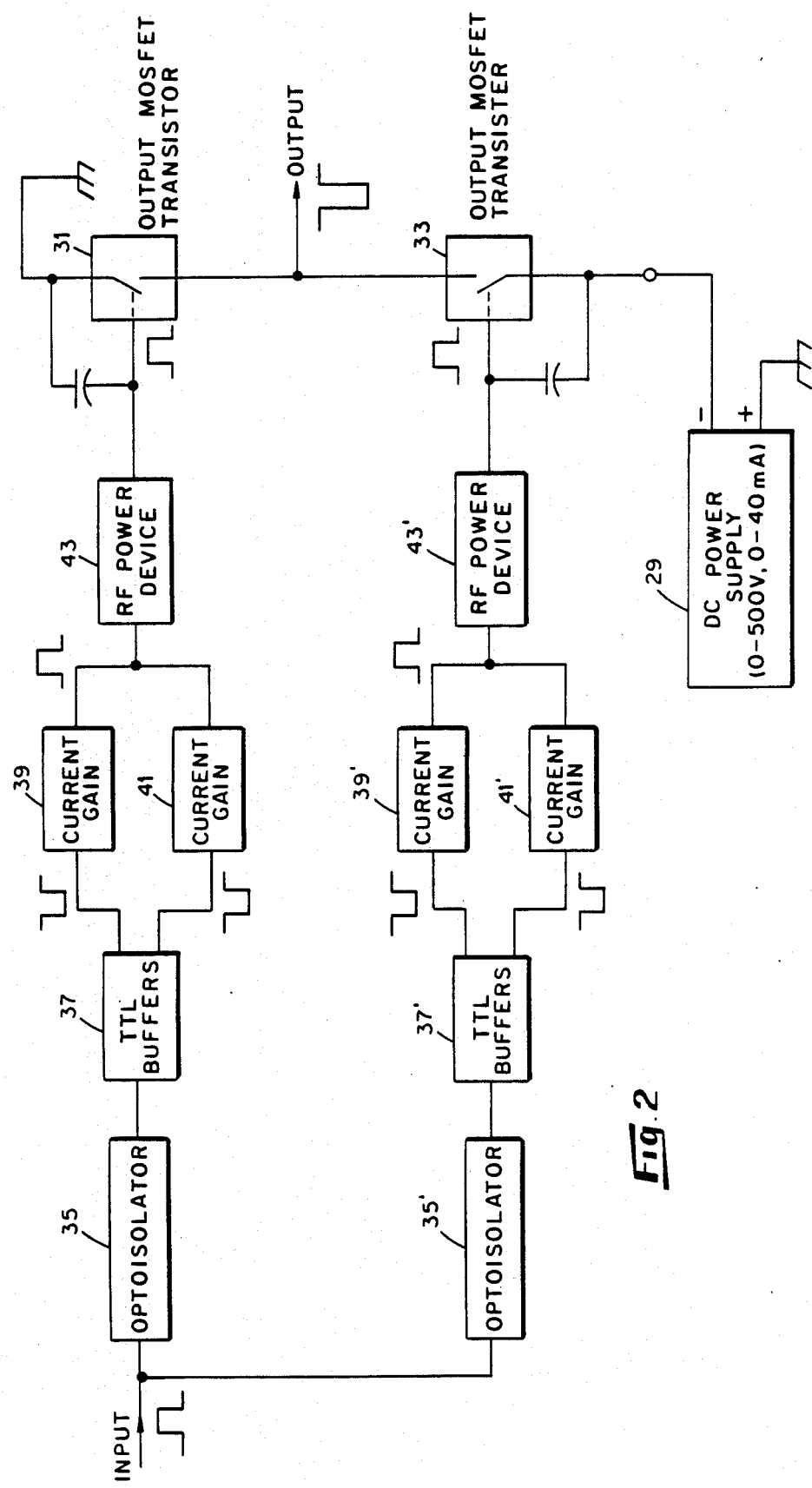
FIG. 2 is a block diagram of the high voltage pulser shown in block form in FIG. 1.
Figure 3:
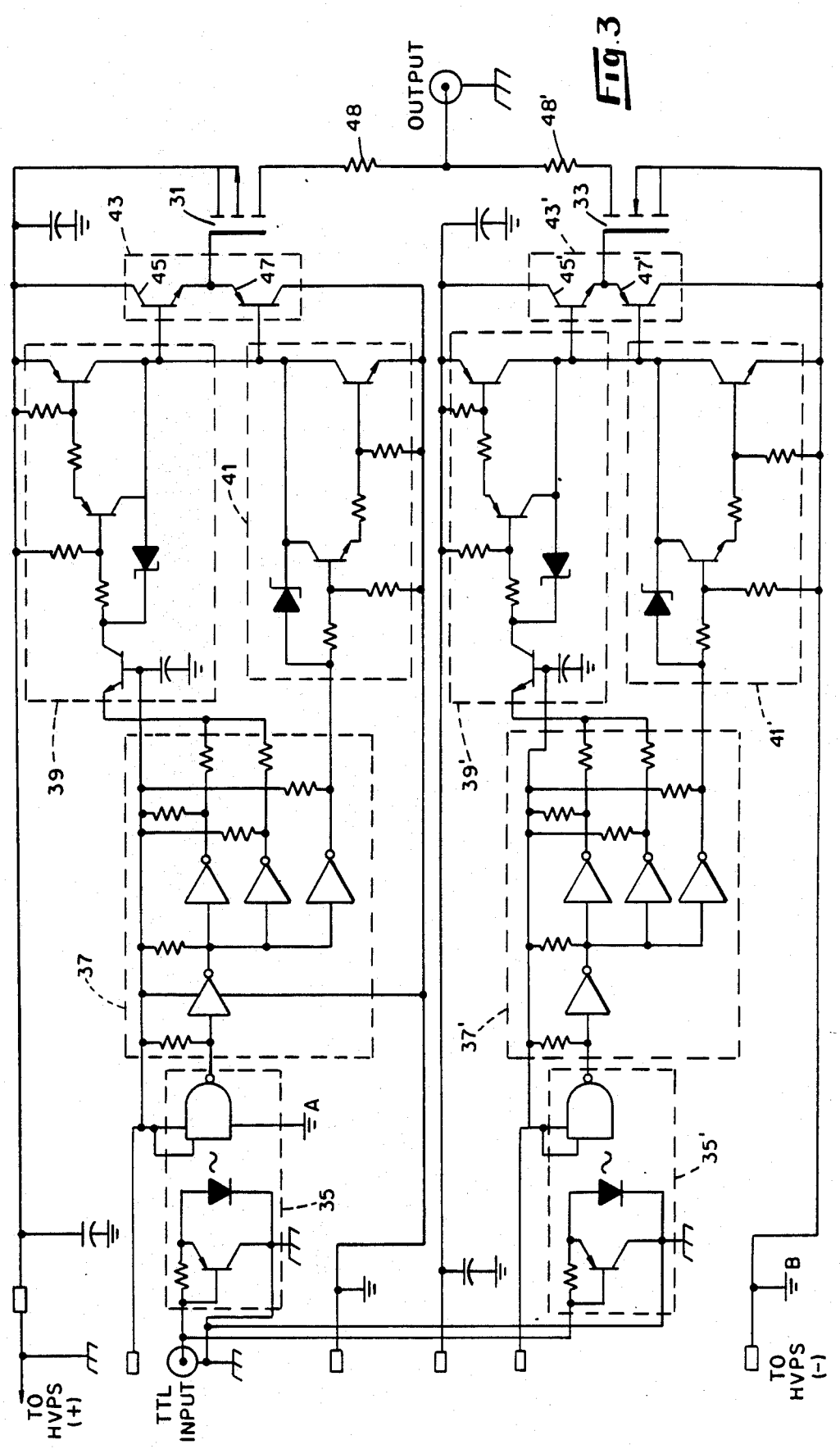
FIG. 3 is a schematic diagram of the high voltage pulser shown in block form in FIG. 2.

The pulser 25 is shown in block diagram form in FIG. 2 and in schematic diagram form in FIG. 3. The schematic portions of the circuit in FIG. 3 corresponding to the blocks shown in FIG. 2 are enclosed by dashed lines and numbered to correspond to the blocks of FIG. 2. The circuitry consists of dual gate-drive channels to switch the output either to ground or to the selected negative high-voltage level. To drive high-voltage pulses of various widths and at level amplitudes requires dc coupling at the output. The output devices are complementary MOSFET transistors 31 (MTP2P50) and 33 (1RF830) that have 500 V breakdown ratings. The "on" resistance of these devices is quite low (typically 4 ohms and 1.3 ohms, respectively), and they exhibit no charge storage effects typical of bipolar devices to impair switching speed. The output pulse rise time of about 50 nsec is dominated primarily by the output resistors 48 (FIG. 3) and the cable plus detector capacitances. The output devices are driven out of phase, so that only one device is on at a time. Since the input gate capacitance of the transistors is large (600–1,000 pF), high current drivers are required to switch the gates quickly.

Each of the drive channels are essentially identical and thus only the driver circuit for transistor 31 will be described. Like prime reference numerals are used to indicate identical elements in the output transistor 33 driver channel. The TTL pulses from the pulse generator 27 (FIG. 1) are applied to an optoisolator circuit 35 which provides level shifting of the generator pulses to the high output voltage level. The output of the optoisolator 35 is connected to TTL buffer circuits 37 which are used to "square up" the pulse and provide additional current drive to the following stages.

The negative going outputs of the buffer circuits 37 are connected to separate current gain and inverting circuits 39 and 41 which together produce sufficient current gain to drive the large input capacitance of the MOSFET 31 quickly through a coupling RF power device 43.

As shown in FIG. 3, the current gain circuits 39 and 41 are formed of non-saturating Darlington inverters which provide extremely fast, high current switching of the MOSFET 31 through bipolar radio frequency power transistors 45 and 47. Thus, when a positive going reference pulse from the pulse generator 27 is applied to the input of the pulser a corresponding width pulse is produced at the output due to transistor 31 being switched "off" and transistor 33 being switched "on". The output pulse has an amplitude corresponding to the selected negative voltage applied from the variable dc power source 29. The voltage applied to the HID is not distorted or reduced in amplitude by the loading effects of the cable connectors and detector capacitance because of the low output impedance of the pulser. Overall, the pulser provides the unique feature of high frequency switching at high voltages, up to 333 kHz at 500 V.

Figure 4:
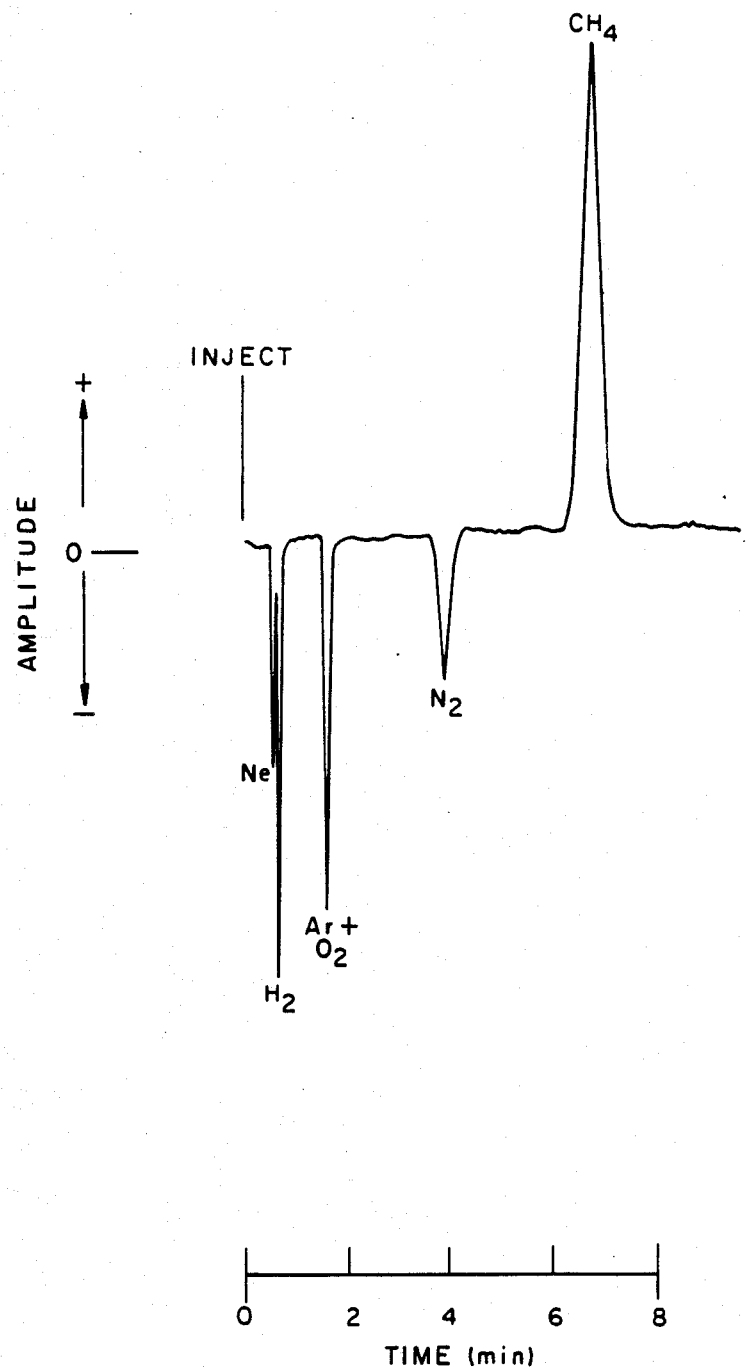
FIG. 4 is a graph of the detector current amplitude response for a standard gas mixture ambient column temperature and the detector pulsed at a frequency of 20 kHz with a duty cycle of 80% and a pulse amplitude of 350 V.

The response characteristics of the pulsed HID were examined by analyzing a standard gas mixture containing 7.6 ppm $H_2$, 7.6 ppm $CH_4$, 8.0 ppm $N_2$, 7.5 ppm $O_2$, 7.5 ppm Ne, and 7.8 ppm Ar in ultrapure helium, at various frequencies and duty cycles. The chromatogram shown in FIG. 4 was obtained at 350 V, 20 kHz and 80% duty cycle. The response to Ne, $H_2$, Ar+$O_2$, and $N_2$ was negative which is characteristic of an HID when ultrapure helium (99.9999%) is used as the carrier gas. Argon and $O_2$ were not resolved on the analytical separation column used. Separations were carried out in a 1.8 m ×2.1 mm I.D., 3.2 mm O.D. stainless steel column, packed with molecular seive 5 A (80–100 mesh). The column was operated isothermally at room temperature. The carrier gas was introduced at a flow rate of approximately 35 ml/min. The magnitude of the response for $CH_4$ was approximately 50% of that obtained at 350 V dc, while the other gases gave about 30% of their response at dc conditions. However, the noise level was substantially reduced in the pulsed mode (i.e., by a factor of 3 under the given conditions) and the detector background current was approximately half.

Further, frequency effects were examined from 0.8 to 400 kHz at 80% duty cycle with 350 V pulses at the detector. The greatest response for all the gases examined was obtained at the highest frequency. Noise levels in all cases were less than in the conventional dc mode. At 400 kHz, $CH_4$ gave 76% of the dc signal and the noise level was reduced by 50%. It was also determined that the detector could be used at higher voltages than possible with dc operation before the detector current would break down. The pulsed detector could be operated up to 500 V at 333 kHz while in the dc mode the detector could be only operated up to 460 V. Since the response increases exponentially at higher voltages, operation under these conditions should provide significant increases in sensitivity. The highest response for all gases tested was obtained at high frequencies and high duty cycle combinations.

In addition it was discovered that at certain frequencies and duty cycles an inversion of the signal polarity for $H_2$, Ar+$O_2$, and $N_2$ was obtained. Reversals for one or more peaks occurred within the range of 3 to 45 kHz when the duty cycles were less than 60%. The magnitude of the inverted responses was also found to increase exponentially with increasing voltage. With the conventional HID the upper detection limit for these gases is only approximately 100 ppm. Higher levels produce deformed W-shaped peaks. Inverting the peaks to positive improves the upper detection limit.

Depending upon the analytical requirements then, the response may be easily adjusted to cover a broad range simply by varying the frequency and/or duty cycle. For high sensitivity operation, high frequency voltage and duty cycles are required while high concentrations (>100 ppm) $H_2$, Ar, $O_2$, and $N_2$ are best analyzed at low duty cycles and frequencies.

We claim:

1. A pulsed helium ionization detection system, comprising:
   an ionization detection chamber including anode and cathode electrodes between which helium carrier gas containing an ionizable component to be detected is introduced and an ionizing radiation source disposed within said chamber for ionizing only said component to be detected;
   ionization current sensing means for sensing and recording the magnitude of ionization current produced by the ionization of said component to be detected in said detection chamber as a direct indication of the concentration of said ionizable component introduced into said chamber; and
   a high voltage pulser means for generating and applying bias voltage pulses at selected frequencies over a range of from about 1 kHz to 333 kHz, amplitudes up to about 500 volts and duty cycles to produce a discontinuous ionization current output sensed by said ionization current sensing means.

2. The system as set forth in claim 1 wherein said high voltage pulser means includes a variable high voltage dc power source for producing output voltages over a selectable range up to about 500 volts, a reference pulse generator means for providing variable frequency and pulse width reference pulses at an output thereof, and a high voltage switching means operable in response to said reference pulses at the output of said reference pulse generator means and the output voltage of said dc power source for generating said bias voltage pulses at an output thereof having an amplitude corresponding to the selected output of said power source and frequency and width corresponding to the width of said reference pulses from said reference pulse generator means.

3. The system as set forth in claim 2 wherein said high voltage switching means includes first and second complementary MOSFET transistors connected in series outposition between the output of said high voltage power supply and ground potential so that the common connecting point of said first and second MOSFET transistors forms the output of said high voltage switching means and first and second high-current gain gate drive channels connected between the output of said reference pulse generator means and the gate electrodes of said first and second MOSFET transistors, respectively, so that said output of said switching means is alternately switched between the output of said high voltage power supply and ground potential at a frequency corresponding to the selected frequency of the output of said reference pulse generator means.

4. The system as set forth in claim 3 wherein said ionizing radiation source is a 1 Ci scandium tritide source and wherein the width of said pulses at the output of said switching means may be varied over a range of from 150 n sec to about dc conditions.

* * * * *